US012740714B2

(12) United States Patent
Bush et al.

(10) Patent No.: US 12,740,714 B2
(45) Date of Patent: Sep. 22, 2026

(54) METHOD AND APPARATUS HAVING PHOTOACOUSTIC PATCH WITH SPHYGMOMETER FOR AUTOMATED BLOOD PRESSURE MONITORING

(71) Applicant: THE JOHNS HOPKINS UNIVERSITY, Baltimore, MD (US)

(72) Inventors: Brian Peter Bush, Baltimore, MD (US); Emad Boctor, Ellicott City, MD (US); Laeben C. Lester, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/712,029

(22) PCT Filed: Nov. 14, 2022

(86) PCT No.: PCT/US2022/049826
§ 371 (c)(1),
(2) Date: May 21, 2024

(87) PCT Pub. No.: WO2023/107246
PCT Pub. Date: Jun. 15, 2023

(65) Prior Publication Data

US 2025/0000366 A1 Jan. 2, 2025

Related U.S. Application Data

(60) Provisional application No. 63/288,065, filed on Dec. 10, 2021.

(51) Int. Cl.
*A61B 5/00* (2006.01)
*A61B 5/02* (2006.01)
(Continued)

(52) U.S. Cl.
CPC ........ *A61B 5/0095* (2013.01); *A61B 5/02028* (2013.01); *A61B 5/02125* (2013.01);
(Continued)

(58) Field of Classification Search
CPC ............. A61B 5/0095; A61B 5/02028; A61B 5/02125; A61B 5/02225; A61B 5/029;
(Continued)

(56) References Cited

U.S. PATENT DOCUMENTS

2005/0143640 A1 6/2005 Hoctor et al.
2011/0071598 A1 3/2011 McKenna
(Continued)

OTHER PUBLICATIONS

Lindner, N. (Authorized officer), International Preliminary Report on Patentability in corresponding International Application No. PCT/US2022/049826 mailed on Jun. 20, 2024, 8 pages.
(Continued)

*Primary Examiner* — Serkan Akar
(74) *Attorney, Agent, or Firm* — MH2 Technology Law Group LLP

(57) ABSTRACT

Several methods of automatically measuring blood pressure are disclosed, which may include applying a photoacoustic imaging band or patch coupled to a transducer or detector capable of detecting an imaging signal to an extremity of a patient. The detector may also include an ultrasonic or photoacoustic means of determining blood pressure. A device for automatically measuring blood pressure utilizing several methods and having a variety of configurations for obtaining blood pressure data from a patient is also disclosed.

15 Claims, 9 Drawing Sheets

(51) Int. Cl.
*A61B 5/021* (2006.01)
*A61B 5/022* (2006.01)
*A61B 5/029* (2006.01)
*A61B 5/1455* (2006.01)

(52) U.S. Cl.
CPC .......... *A61B 5/02225* (2013.01); *A61B 5/029* (2013.01); *A61B 5/14551* (2013.01); *A61B 5/6814* (2013.01); *A61B 5/6822* (2013.01); *A61B 5/6824* (2013.01); *A61B 5/6831* (2013.01); *A61B 5/6833* (2013.01); *A61B 2560/045* (2013.01); *A61B 2560/0462* (2013.01)

(58) Field of Classification Search
CPC . A61B 5/14551; A61B 5/6814; A61B 5/6822; A61B 5/6824; A61B 5/6831; A61B 5/6833; A61B 2560/045; A61B 2560/0462; A61B 5/02055; A61B 5/681; A61B 5/742; A61B 5/0261; A61B 5/021
See application file for complete search history.

(56) References Cited

U.S. PATENT DOCUMENTS

| | | | | |
|---|---|---|---|---|
| 2013/0184544 | A1 | 7/2013 | Su et al. | |
| 2014/0180030 | A1 | 6/2014 | Dorando | |
| 2014/0194740 | A1* | 7/2014 | Stein | A61B 8/565 600/455 |
| 2018/0064346 | A1 | 3/2018 | Zheng et al. | |
| 2021/0022623 | A1 | 1/2021 | Rice et al. | |
| 2022/0175258 | A1* | 6/2022 | Kitchens | A61B 5/02116 |
| 2022/0338841 | A1* | 10/2022 | Bell | G01S 7/52046 |
| 2023/0363711 | A1* | 11/2023 | Theodore | A61B 5/0031 |
| 2023/0371901 | A1* | 11/2023 | Manbachi | A61B 8/04 |
| 2023/0404473 | A1* | 12/2023 | Theodore | A61N 1/36014 |

OTHER PUBLICATIONS

Rodriquez, K. (Authorized officer), International Search Report and Written Opinion in corresponding International Application No. PCT/US2022/049826 mailed on Mar. 3, 2023, 9 pages.

* cited by examiner

METHOD AND APPARATUS HAVING PHOTOACOUSTIC PATCH WITH SPHYGMOMETER FOR AUTOMATED BLOOD PRESSURE MONITORING

REFERENCE TO RELATED APPLICATIONS

This application is the national stage entry of International Patent Application No. PCT/US2022/049826, filed on Nov. 14, 2022, and published as WO 2023/107246 A1 on Jun. 15, 2023, which claims the benefit of U.S. Provisional Patent Application No. 63/288,065, filed on Dec. 10, 2021, which are hereby incorporated by reference in their entireties.

TECHNICAL FIELD

The present teachings relate generally to blood pressure monitoring and, more particularly, to blood pressure monitoring with the use of photoacoustics and methods thereof.

BACKGROUND

Automated non-invasive blood pressure monitoring is an essential component of modern medical management and measures an important vital sign. Current oscillometric automated blood pressure cuffs have several limitations. Oscillometric blood pressure cuffs perform poorly in obese patients, patients with severe vascular disease, and during episodes of low blood pressure. Furthermore, they do not directly measure systolic blood pressure, but rather estimate it from the mean arterial pressure (MAP). Accurate non-invasive blood pressure monitoring in subjects with non-pulsatile flow, such as those with left ventricular assist devices (LVAD) or on veno-arterial extracorporeal membrane oxygenation (VA-ECMO) can also be challenging.

In patients with non-pulsatile flow, non-invasive blood pressure is usually obtained with multiple devices, such as an audible hand-held vascular Doppler with a manual sphygmometer. The hand-held vascular Doppler is placed over the presumed location of an artery and adjusted until arterial flow is audible. The sphygmometer is inflated until the sound goes away, and then slowly deflated. The pressure at which the sound returns (or disappears) is generally referred to as the mean arterial pressure (MAP). In critically ill patients or those undergoing anesthesia, frequent blood pressure measurement can be difficult because any movement of the patient or measurement apparatus can result in loss of the signal, even after the location is marked on the skin. Thus, it may be sometimes unclear if the Doppler simply moved and can be realigned for repeat measurement (a frequent occurrence), or if the patient has lost a perfusing blood pressure and is in fact in a state equivalent to pulseless electrical activity (a rare occurrence). Therefore, one or more invasive arterial lines are often placed even for short elective procedures. However, because patients with LVADs are medically fragile and require frequent procedures such as upper and lower endoscopy, multiple arterial line placements lead to scarring, making monitoring increasingly difficult or impossible in the future and compromising blood flow to extremities. More than 50 million surgeries are performed each year in the United States, and 234 million globally. Furthermore, more than 25,000 LVADs have been implanted in the US with greater than 2,500 new implants per year. In a given year, close to 16% of these patients undergo surgery. Therefore, it would be beneficial to have a minimally invasive device and methods for continuous automated blood pressure monitoring of patients during various procedures and/or in various stages of care.

SUMMARY

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

A method of automatically measuring blood pressure is disclosed. The method of automatically measuring blood pressure includes applying a photoacoustic imaging band to an extremity of a patient. The method of automatically measuring blood pressure also includes contacting the photoacoustic imaging band to a location on the extremity adjacent to a location of a vessel of interest. The method of automatically measuring blood pressure also includes delivering energy to the extremity with the photoacoustic imaging band at the location of the vessel of interest. The method of automatically measuring blood pressure also includes receiving a detectable imaging signal from analyzing a detected image from the vessel of interest, and analyzing the imaging signal and the delivered energy to determine blood flow and blood pressure.

Implementations may include where the location on the extremity is overlying a presumed location of a brachial artery or a presumed location of a radial artery. The method of automatically measuring blood pressure may include measuring a non-pulsatile flow with a sphygmometer cuff. The method of automatically measuring blood pressure may include measuring a pulsatile flow with a sphygmometer cuff. The method of automatically measuring blood pressure may include receiving a pulse wave velocity signal or receiving a continuous wave signal. The method of automatically measuring blood pressure may include transmitting blood pressure information to an external device. The method of automatically measuring blood pressure may include measuring blood flow, pulse oximetry, hemoglobin, changes in blood pressure size, or a combination thereof, or estimating stroke volumes, cardiac output, systemic vascular resistance, pulse pressure variation, systolic pressure variation, or a combination thereof using waveform analysis.

A method of automatically measuring blood pressure is disclosed, including applying a photoacoustic imaging patch to an extremity of a patient. The method of automatically measuring blood pressure also includes contacting the photoacoustic imaging patch to a location on the extremity adjacent to a location of a vessel of interest. The method of automatically measuring blood pressure also includes delivering energy to the extremity with the photoacoustic imaging patch at the location of the vessel of interest. The method also includes receiving a detectable imaging signal from analyzing a detected image from the vessel of interest and analyzing the imaging signal and the delivered energy to determine blood flow and blood pressure.

Implementations may include where the patch is applied to the extremity with the use of a temporary adhesive. The method of automatically measuring blood pressure may include measuring blood flow, pulse oximetry, hemoglobin, changes in blood pressure size, or a combination thereof, or estimating stroke volumes, cardiac output, systemic vascular resistance, pulse pressure variation, systolic pressure variation, or a combination thereof using waveform analysis.

An automated blood pressure monitoring device is also disclosed. The automated blood pressure monitoring device includes a photoacoustic element coupled to a band. The device also includes an ultrasound transducer coupled to and disposed in a position in adjacent to the photoacoustic element. The automated blood pressure monitoring device may include a pressure cuff coupled to and adjacent to the photoacoustic element.

An automated blood pressure monitoring device is disclosed. The automated blood pressure monitoring device also includes a photoacoustic element coupled to a patch. The device also includes an ultrasound transducer coupled to and disposed in a position in adjacent to the photoacoustic element. The automated blood pressure monitoring device may include a pressure cuff coupled to and adjacent to the photoacoustic element.

An automated blood pressure monitoring device is disclosed. The automated blood pressure monitoring device also includes a sphygmometer having a pressure cuff, and a photoacoustic element coupled to and in a position adjacent to the pressure cuff. The automated blood pressure monitoring device may include where the photoacoustic element is coupled to a band. The photoacoustic element is coupled to a patch. The patch further may include a layer of temporary adhesive.

BRIEF DESCRIPTION OF THE DRAWINGS

The accompanying drawings, which are incorporated in and constitute a part of this specification, illustrate embodiments of the present teachings and together with the description, serve to explain the principles of the disclosure. In the figures.

Figure 1A:
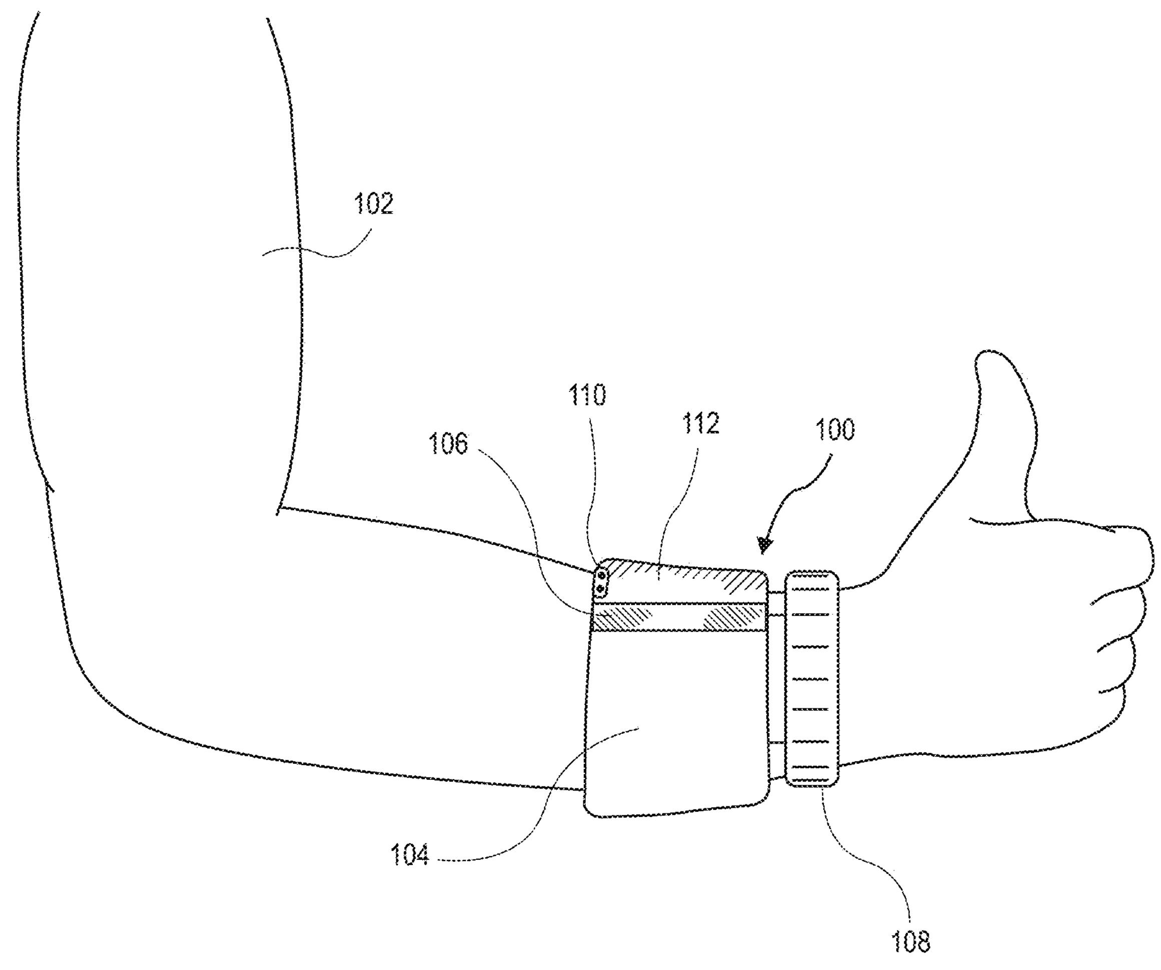
FIG. 1A is a schematic view of an automated blood pressure monitoring device using pressure measurement and a detector shown in place on a patient being measured with the data being transmitted wirelessly, according to an embodiment.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same, similar, or like parts.

Bedside ultrasound machines that include color flow Doppler for vascular identification are now ubiquitous in the operating room, emergency department, and ICU. Because of the difficulty associated with identifying arterial flow with audible handheld vascular Doppler, color flow Doppler ultrasound is more capable of identifying brachial and/or radial arteries and other vessels in patients, particularly in patients having conditions such as LVAD to facilitate audible handheld Doppler placement for non-invasive blood pressure monitoring. It has also been established that both the handheld vascular Doppler reporting the signal as a sound signal and the color flow Doppler reporting the signal as color on an image measure the same Doppler signal. Furthermore, color flow Doppler ultrasound can be significantly easier in terms of identifying and maintaining the Doppler signal as compared to audible handheld vascular Doppler ultrasound. Due to the ease of obtaining a signal using color flow Doppler with ultrasound this may be used in conjunction with adjunct measurement devices or methods to facilitate blood pressure measurement in patients with LVAD undergoing anesthesia and with other complications or states of care. These automated blood pressure measurements utilizing color flow Doppler measurement methods should correlate with the more invasive yet accurate method of arterial line pressure monitoring. Additionally, photoacoustic imaging devices may also work in concert with any of the aforementioned devices or methods in less invasive integrated measurement devices for automatic blood pressure detection.

Embodiments of the devices disclosed herein have the capability of more accurately measuring systolic blood pressure in all patients and offer continuous blood pressure estimates. In embodiments described herein, the blood pressure in patients with low flow states, including LVADS and VA-ECMO may be measured via non-invasive measurement. Devices as described herein may also enable direct visualization of flow in the artery, as well as arterial caliber and other patient vital signs and measurements. In an embodiment described herein, an automated blood pressure measurement device band using photoacoustics, including measurements of pulse wave, continuous wave, strain and area change, or combinations thereof. In addition, the utilization of 3D ultrasound may further enhance function. The device, according to embodiments, may include a pressure inducing element, such as a sphygmometer or sphygmomanometer or sphygmometer cuff, tonometer, or combinations thereof, coupled with the photoacoustic transducer that contacts the skin on the extremity adjacent to the pressure measuring element. The cuff or pressure inducing element and ultrasonic transducer, or light source and detector are positioned such that the transducer or device is overlying the presumed location of the brachial or radial artery, as well as other target vessels of the lower extremity or in other anatomical locations, such as the neck of a patient (carotid artery) or head (middle cerebral artery). Such a device automatically measures, recognizes, and analyzes an arterial and blood flow signal by Doppler, including color flow, pulse wave velocity, and continuous measurements, and changes in blood vessel size. In certain embodiments, a sphygmometer cuff may inflate until there is no longer a measurable flow through the artery, then it will deflate until a color flow signal is once again measurable. Next, the flow patterns may be analyzed to determine mean and diastolic blood pressure, among other patient vital signs. Devices utilizing photoacoustic measurement may measure pulse oximetry, hemoglobin, and temperature. Certain embodiments of devices as described herein can be utilized to estimate arterial flow, cardiac output, and systemic vascular resistance. Certain embodiments may also include continuous wave doppler in order to more accurately determine, and coordinate with known pressure application from the device, the systolic and diastolic pressure of the patient. In a case of non-pulsatile flow in a patient, the pressure at which flow returns could be measured and displayed as the mean arterial pressure (MAP) for either the caregiver or the device user. According to other embodiments, the application of non-occlusive pressure in conjunction with a doppler waveform may be used to estimate a continuous blood pressure waveform, and allows for estimation of cardiac output, systemic vascular resistance (SVR), and other measurements. In certain embodiments, an output ultrasound image and waveform can be displayed visually in a monitor as part of the device, allowing for important confirmation and feedback of hemodynamic status by a clinician or other user of the device. In general, a first embodiment involves inflating a cuff, band, or patch affixed to a patient with a layer of a temporary adhesive, or other pressure inducing or measuring component to measure blood pressure in a vessel of interest by a detector capable of interpreting, analyzing, and/or calculating blood pressure from a detected image. Another embodiment involves measuring and detecting a partially occlusive flow in a vessel of interest. Certain embodiments may not include a cuff or patch or direct pressure measuring element, instead utilizing photoacoustic or ultrasonic energy mathematically derive a blood pressure signal from flow velocities within a vessel of interest, thereby determining blood flow and related vital patient data from the data and acquired imaging information. In some cases, a blood pressure cuff or other measuring device may be added to improve reliability of the measurement. Transmission of acquired, analyzed or directly measured blood pressure and other vital sign data may be transmitted to a de-localized or remote location to provide blood pressure or patient vital sign information to an internal or external display, physician's office, a nurse's station, home health monitoring hub, other medical data center, and the like, or combinations thereof.

FIG. 1A is a schematic view of an automated blood pressure monitoring device using pressure measurement and a detector shown in place on a patient being measured with the data being transmitted wirelessly, according to an embodiment. A blood pressure monitoring device 100 which defines a cuff to measure pressure 104 is fastened onto or around an extremity of a patient 102, in this case near or around the wrist of a patient 102. The cuff to measure pressure 104 also includes a central processing unit 106 contained either internal to or on an external surface of the cuff 104. The cuff 104 also includes a charging plug 110 and a battery 112, and includes or is attached to a detector 108. The detector 108 may be either ultrasonic or photoacoustic in nature, and senses, receives, or creates a response by a vessel of interest adjacent to the placement of the blood pressure monitoring device 100 that may be interpreted and analyzed by the central processing unit 106 to generate and/or analyze an image to determine various parameters within a patient's vessel of interest to determine a blood pressure reading, as well as other vital signs. Additional vital signs that may be measured, received, analyzed, interpreted, estimated, or a combination thereof include blood pressure, heart rate, blood vessel size, pulse oximetry, hemoglobin level, temperature, cardiac output, cardiac index, or systemic vascular resistance. The detector 108 may also receive or generate pulse wave velocity from the vessel of interest from which a mathematical derivation may calculate blood pressure of a patient 102. In a typical operation sequence, the cuff 104 is inflated to measure blood pressure, and the detector 108 measures the pressure. While the inflation step of the cuff 104 is not required, its use may improve overall reliability of the blood measure measurement. The pressure cuff may be a sphygmometer or other pressure measurement device. The sensor or detector 108 could be photoacoustic based, low frequency ultrasonic based, high frequency ultrasound based, or a combination thereof. The detector 108 may be configured to detect flow in a vessel of interest, which could be, but is not limited to, a brachial or radial artery, for example. While not explicitly shown in FIG. 1A, the blood pressure monitoring device 100 is wirelessly connected to a data receiving device, such as a portable computing device, a display device, a separate computer, or a combination thereof. The communication protocol used between the blood pressure monitoring device 100 and the data receiving device may be wireless wi-fi, cellular, Bluetooth, near field communication (NFC), other wireless communication protocol, or a combination thereof.

Figure 1B:
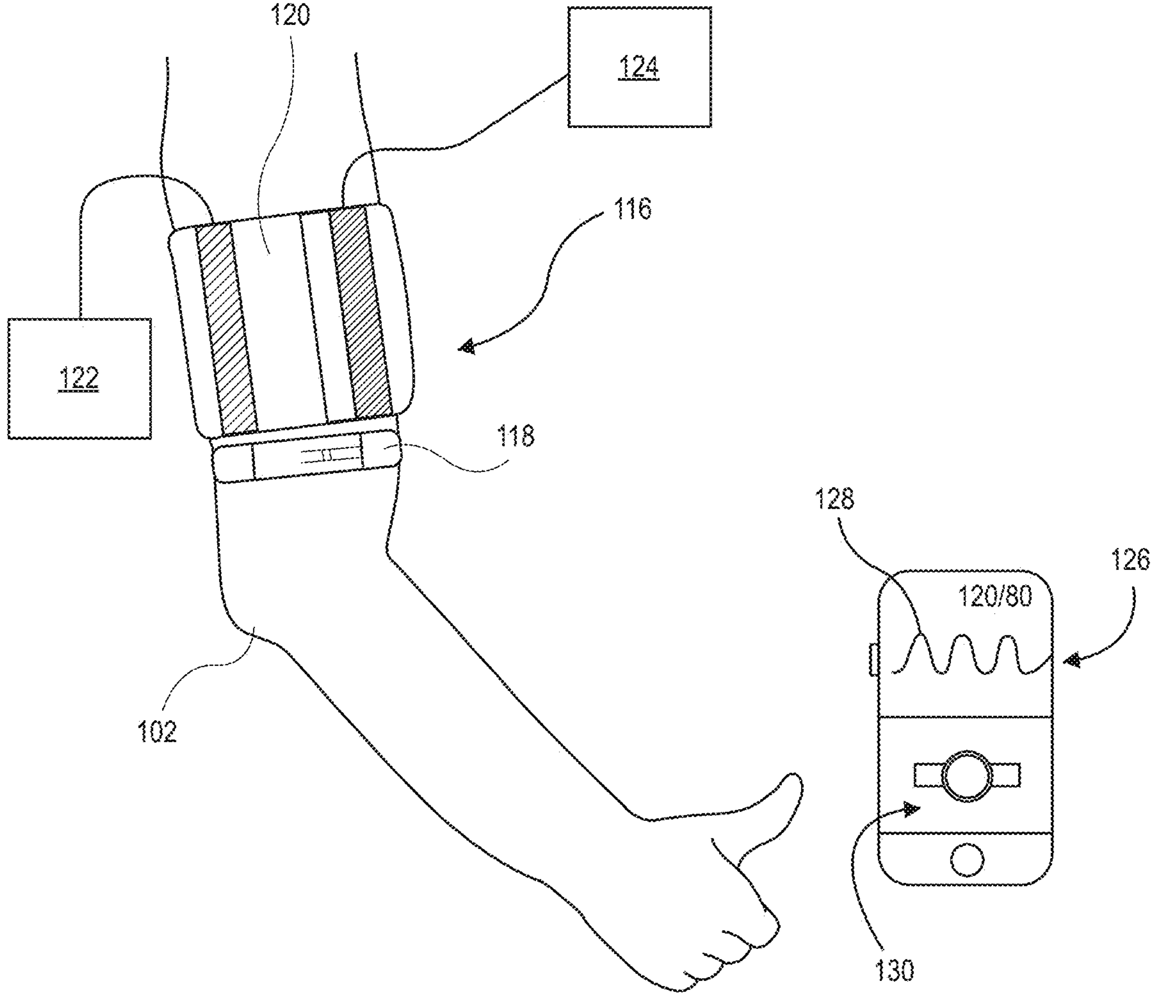
FIG. 1B is a schematic view of an automated blood pressure monitoring device using pressure measurement and a detector shown in place on a patient being measured with the data being transmitted wirelessly, according to an embodiment.

FIG. 1B is a schematic view of an automated blood pressure monitoring device using pressure measurement and a detector shown in place on a patient being measured with the data being transmitted wirelessly, according to an embodiment. An automated blood pressure monitoring device 116 is illustrated in FIG. 2B, similar to the automated blood pressure monitoring device shown in FIG. 1A but placed on the upper arm of a patient 102. The blood pressure monitoring device 116 includes a digital sphygmometer 120 capable of and configured to apply pressure and enable measurement of blood pressure. Adjacent to and connected to the digital sphygmometer 120 portion of the blood pressure monitoring device 116 is a detector 118, an external battery 122, and an external sphygmometer pump 124. Data measured or acquired from the blood pressure monitoring device 116 may be transmitted wirelessly to a portable computing device 126, and information is displayed on the portable computing device 126, including a display of blood pressure 128 a visual diameter display of vessels 130 being measured, which in this illustration would represent a brachial artery and surrounding veins. The attached detector 118 can be an ultrasound probe or patch to visualize vessel, measure change and flow, and blood pressure. The portable computing device 126 may be a remote wireless monitor, phone, tablet, personal computer, computer terminal or other suitable device.

Figure 1C:
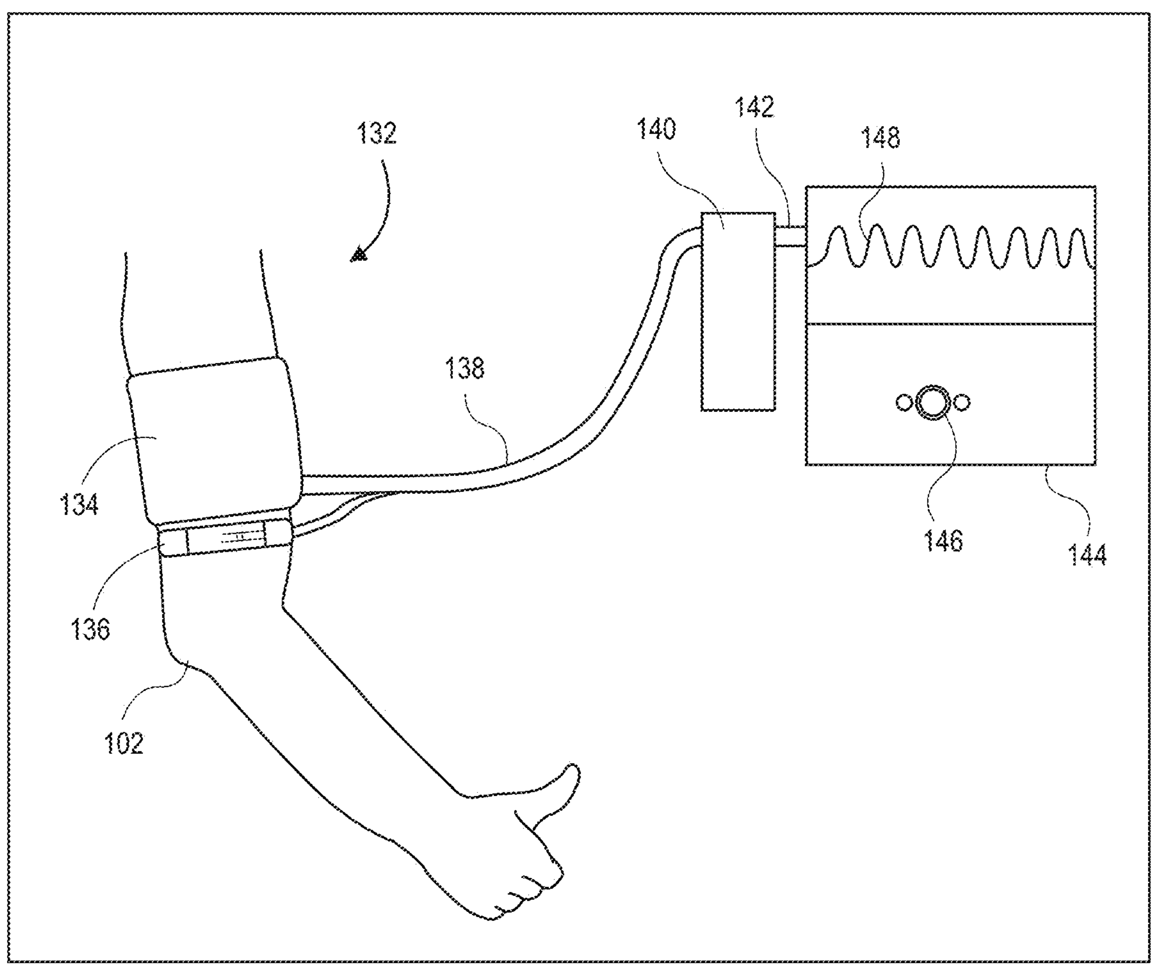
FIG. 1C is a schematic view of an automated blood pressure monitoring device using pressure measurement and a detector shown in place on a patient being measured with the data being transmitted via a wired configuration, according to an embodiment.

FIG. 1C is a schematic view of an automated blood pressure monitoring device using pressure measurement and a detector shown in place on a patient being measured with the data being transmitted via a wired configuration, according to an embodiment. Illustrated in FIG. 1C is another embodiment of the blood pressure monitoring device shown in FIG. 1B including wired connections. The automated blood pressure monitoring device 132 includes a sphygmometer 134 a detector probe 136, both of which are coupled to and connected to external equipment via a wire or connector 138. The attached portion of the blood pressure monitoring device 132 is connected to an external processing unit and sphygmometer pump, and an external battery or power source held within an external instrument housing 140. A second wire or connector 142 connects the housing 140 to a display device 144 which displays a visualization of vessels 146, in this illustration brachial artery and veins, and a display of blood pressure 148. The display device 144 may be connected to an additional phone, tablet, personal computer, computer terminal or other suitable computing or processing device.

Figure 1D:
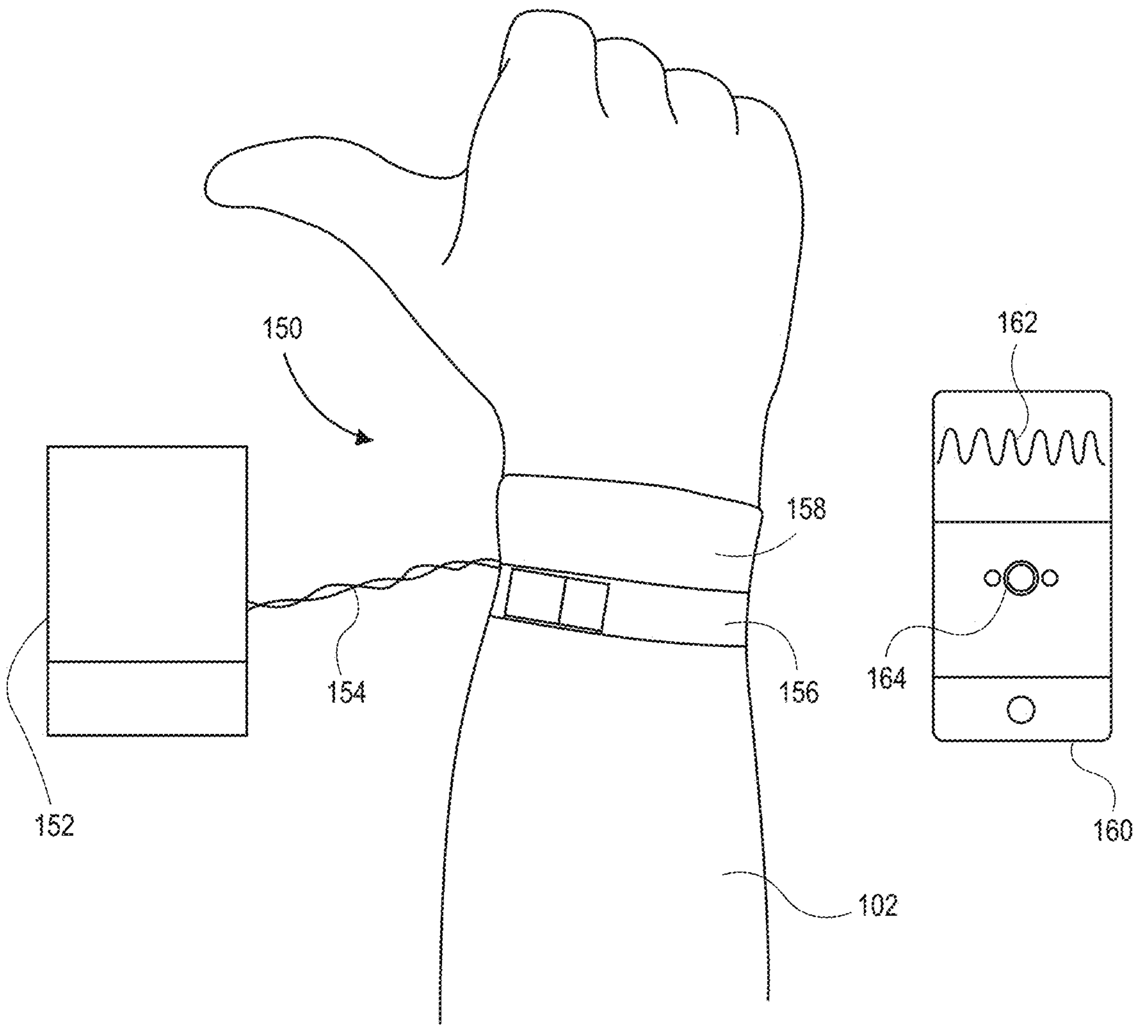
FIG. 1D is a schematic view of an automated blood pressure monitoring device having an external component using a detector shown in place on a patient being measured with the data being transmitted wirelessly, according to an embodiment.

FIG. 1D is a schematic view of an automated blood pressure monitoring device having an external component using a detector shown in place on a patient being measured with the data being transmitted wirelessly, according to an embodiment. The automated blood pressure monitoring device 150 in the form of a band, strap, or wristband, includes a photoacoustic imaging element 156 and a detector 158 worn on the wrist of a patient 102. The photoacoustic imaging element 156 is used to measure pressure and may be fully wrapped around the wrist or other anatomical portion of a patient 102 or may be in a patch form affixed to a patient 102. The blood pressure monitoring device 150 is connected to an external electronics pack 152 which may include a central processing unit, or CPU, a battery or other power source by a wire or connector 154. Blood pressure and other vital sign measurements obtained using the blood pressure monitoring device 150 are transmitted to a portable computing device 160 or display. In this embodiment the portable computing device 160 includes a display. Illustrated on the portable computing device 160 is a visualization of vessels 164, which in this illustration would be a radial artery and adjacent veins. The portable computing device 160 also displays a display of blood pressure 162 as measured by the blood pressure monitoring device 150. While the embodiment shown in FIG. 1D is shown on a wrist, other embodiments may include a capability of the blood pressure monitoring device 150 to be fastened to another extremity or area of a patient near a location of a vessel of interest, or away from another limiting medical procedure. Examples may include, but are not limited to a neck, forearm, bicep, leg, calf, or ankle. Certain embodiments may include a pressure cuff, a sphygmometer having a pressure cuff placed adjacent or near the photoacoustic imaging element 156 to work in concert with the photoacoustic imaging element 156. The photoacoustic imaging element 156 may be attached to, coupled to, integrated with, or a combination thereof to the band or strap used to fasten the blood pressure monitoring device 150 in place near a vessel of interest.

Figure 1E:
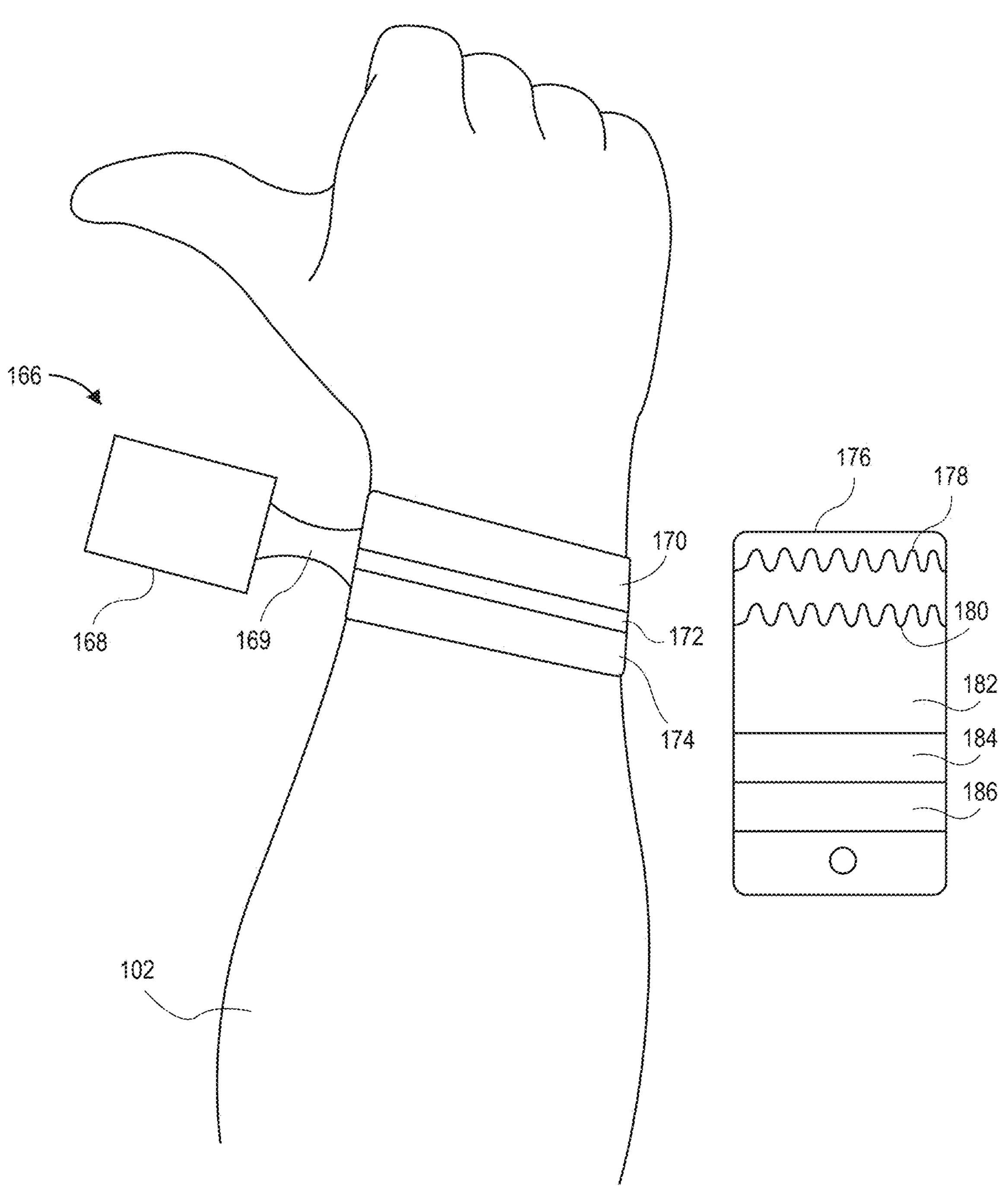
FIG. 1E is a schematic view of an automated blood pressure monitoring device having a detector shown in place on a patient being measured with the data being transmitted wirelessly, according to an embodiment.

FIG. 1E is a schematic view of an automated blood pressure monitoring device having a detector shown in place on a patient being measured with the data being transmitted wirelessly, according to an embodiment. An automated blood pressure monitoring device 166 fastened to a wrist of a patient 102, in a strap or band form as shown in FIG. 1E, includes an integrated detector 170, photoacoustic imaging element 172, and a light source 174 configured to read, measure, or derive blood pressure information from a vessel of interest in a patient 102. The blood pressure monitoring device 166 also includes an external power source 168 connected to the wrist-worn portion including the integrated detector 170, photoacoustic imaging element 172, and a light source 174 by a connector 169. The detector 170 may alternatively be ultrasound or photoacoustic in nature. The light source 174 may be based on light-emitting diodes (LED), halogen lights, or laser. Blood pressure and other vital sign measurements obtained using the blood pressure monitoring device 166 are transmitted to a portable computing device 176 or display. In this embodiment the portable computing device 176 includes a display. Illustrated on the portable computing device 176 is a display of blood pressure 178, display of pulse oximetry 180, display of vital signs 182, such as temperature, hemoglobin level, or venous pressure, a display of blood flow 184, and a second display of vital signs 186 including cardiac output, cardiac index, systemic vascular resistance (SVR), or SVR index. While the embodiment shown in FIG. 1E is shown on a wrist, other embodiments may include a capability of the blood pressure monitoring device 166 to be fastened to another extremity or area of a patient near a location of a vessel of interest, or away from another limiting medical procedure. Examples may include, but are not limited to a neck, forearm, bicep, leg, calf, or ankle. Certain embodiments may include a pressure cuff, a sphygmometer having a pressure cuff placed adjacent or near the photoacoustic imaging element 172 to work in concert with the photoacoustic imaging element 172. The photoacoustic imaging element 172 may be attached to, coupled to, integrated with, or a combination thereof to the band or strap used to fasten the blood pressure monitoring device 166 in place near a vessel of interest.

Figure 1F:
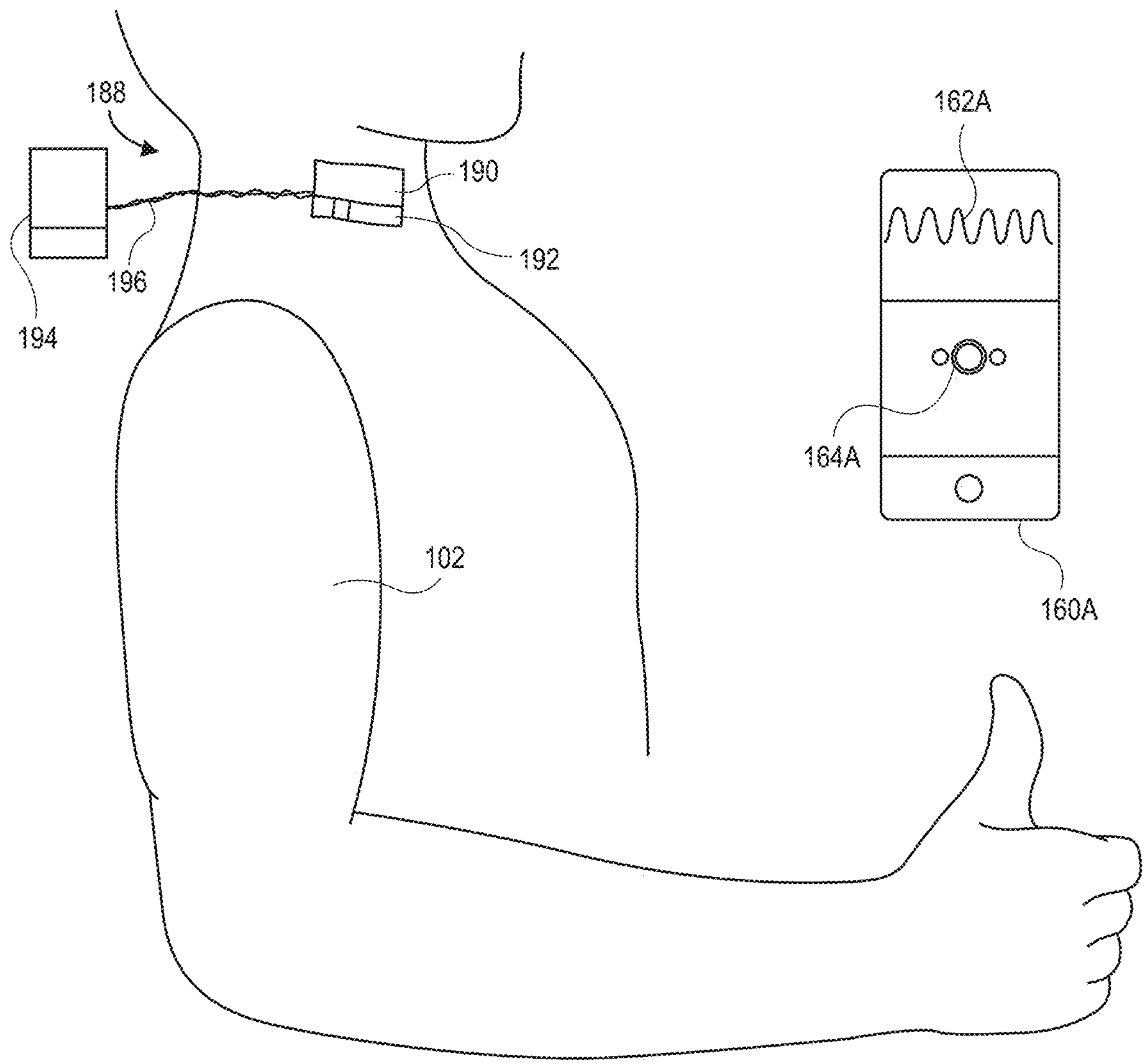
FIG. 1F is a schematic view of an automated blood flow monitoring device having an external component using a detector shown in place on a patient being measured with the data being transmitted wirelessly, according to an embodiment.

FIG. 1F is a schematic view of an automated blood flow monitoring device having an external component using a detector shown in place on a patient being measured with the data being transmitted wirelessly, according to an embodiment. The automated blood flow monitoring device 188 includes a photoacoustic detector 192 which is a component of a patch 190 that is affixed to the neck of a patient 102. The photoacoustic detector 192 used to measure blood flow, either cerebral blood flow or blood flow in a carotid artery, and may be affixed to the neck or other anatomical portion of a patient 102. This may also be affixed to the head/temple to measure blood flow and caliber of the middle cerebral artery. The automated blood flow monitoring device 188 is connected to an external electronics pack 194 which may include a central processing unit, or CPU, a battery or other power source by a wire or connector 196. Blood flow and other vital sign measurements obtained using the automated blood flow monitoring device 188 are transmitted to a portable computing device 160A or display. In this embodiment the portable computing device 160A includes a display. Illustrated on the portable computing device 160A is a visualization of vessels 164A, which in this illustration would be a radial artery and adjacent veins. The portable computing device 160A also displays a display of blood pressure 162A as measured by the automated blood flow monitoring device 188. A separate ultrasonic transducer or other device as described herein may be incorporated or used in conjunction with the automated blood flow monitoring device 188. One example may be a pressure cuff located in another area of the patient and coupled to and in some instances adjacent to the photoacoustic element. In embodiments, the patch further includes a layer of temporary adhesive to affix the patch to the location of interest. While the embodiment shown in FIG. 1F is shown in a neck location, other embodiments may include a capability of the blood flow monitoring device 188 to be fastened to another extremity or area of a patient near a location of a vessel of interest, or away from another limiting medical procedure. Examples may include, but are not limited to a wrist, forearm, bicep, leg, calf, or ankle. Certain embodiments may include accompanying measurement devices as described herein placed adjacent to or near the photoacoustic detector 192 to work in concert with the photoacoustic detector 192. The photoacoustic detector 192 may be attached to, coupled to, integrated with, or a combination thereof to the band or strap used to fasten the blood flow monitoring device 188 in place near a vessel of interest.

Figure 1G:
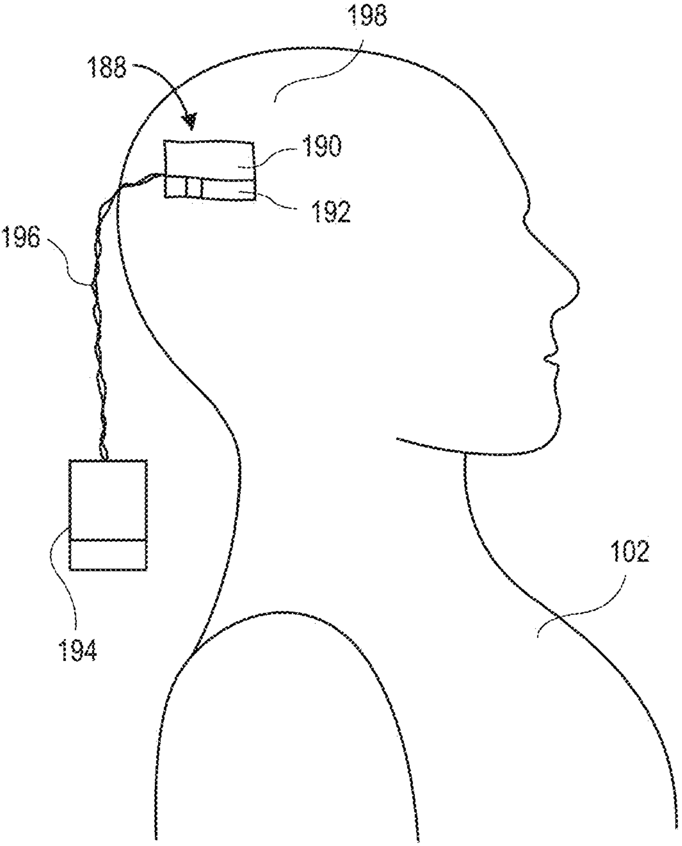
FIG. 1G is a schematic view of an automated blood flow monitoring device having an external component using a detector shown in place on a patient being measured with the data being transmitted wirelessly, according to an embodiment.

FIG. 1G is a schematic view of an automated blood flow monitoring device having an external component using a detector shown in place on a patient being measured with the data being transmitted wirelessly, according to an embodiment. The automated blood flow monitoring device 188 includes a photoacoustic detector 192 which is a component of a patch 190 that is affixed to a head 198 of a patient 102, at or near a location of a temple of the patient 102. The photoacoustic detector 192 used to measure blood flow, either cerebral blood flow or blood flow in a carotid artery, and may be affixed to the head/temple 198 to measure blood flow and caliber of the middle cerebral artery. The automated blood flow monitoring device may be connected to an external device as noted in previous examples herein.

Various sizes and other configurations may be found in certain embodiments. For example, it should be noted that any of the aforementioned components or device elements may be located on the wearable portion of the device itself, i.e., on the cuff or as a wearable watch or wrist strap device. The detector or imaging component may include ultrasound or photoacoustic based imaging devices and/or detectors. The continuous measurement as enabled by such configurations may enhance the fidelity of the blood pressure derivation and/or measurement. Certain embodiments of an apparatus to measure blood pressure may include an inflatable bladder, wrist-worn device including LED, halogen or laser light source. Computer components, power sources, displays, or wireless communications devices may be integrated or external depending on the embodiment. Other pressure inducing or pressure measurement devices may be used in combination with other device elements, such as pressure cuffs, sphygmometers, or other similar devices known to those skilled in the art. Furthermore, the automated devices as described herein may be used in the measurement and evaluation of vasoreactivity, which involves the occlusion of a vessel for a period of time, evaluating, observing, or measuring dynamic parameters of the vessel, such as diameter changes in the vessel as compared to a baseline measurement, to provide an indication of endothelial dysfunction, cardiovascular reserve, or vascular stiffness. Time of inflation during such a measurement, as well as times between baseline measurements and comparative measurements may be important factors in vasoreactivity measurements as described.

Figure 2A:
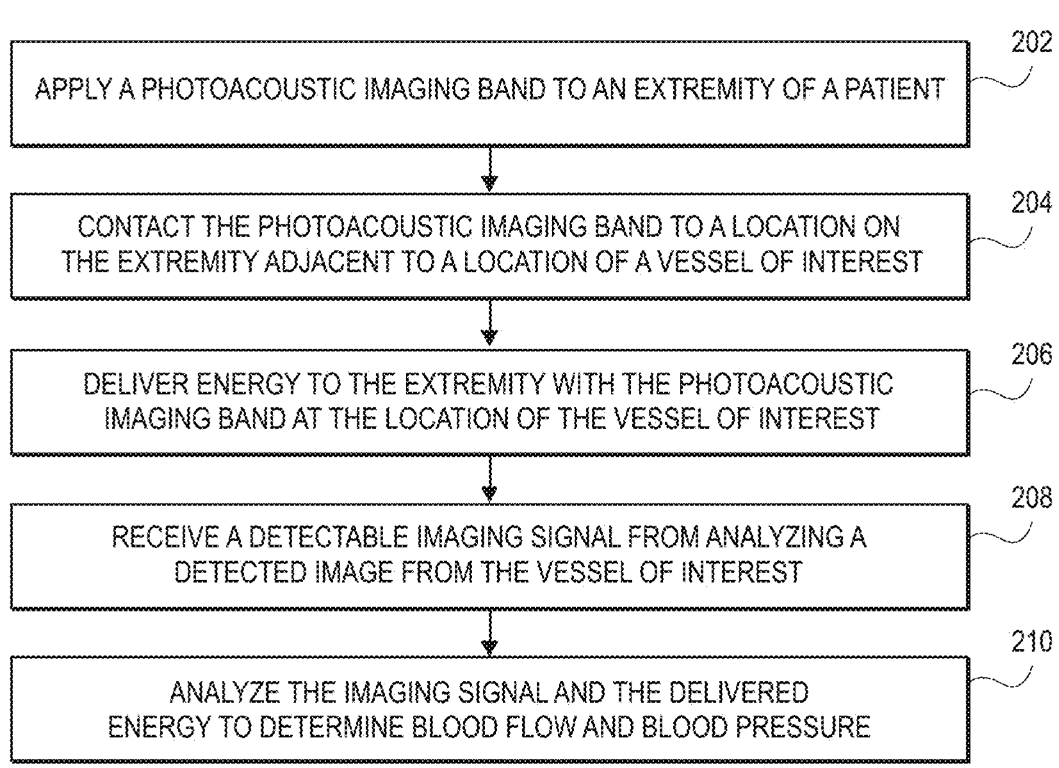
FIG. 2A is a flowchart illustrating an automated method of monitoring blood pressure using photoacoustic detection, according to an embodiment.
Figure 2B:
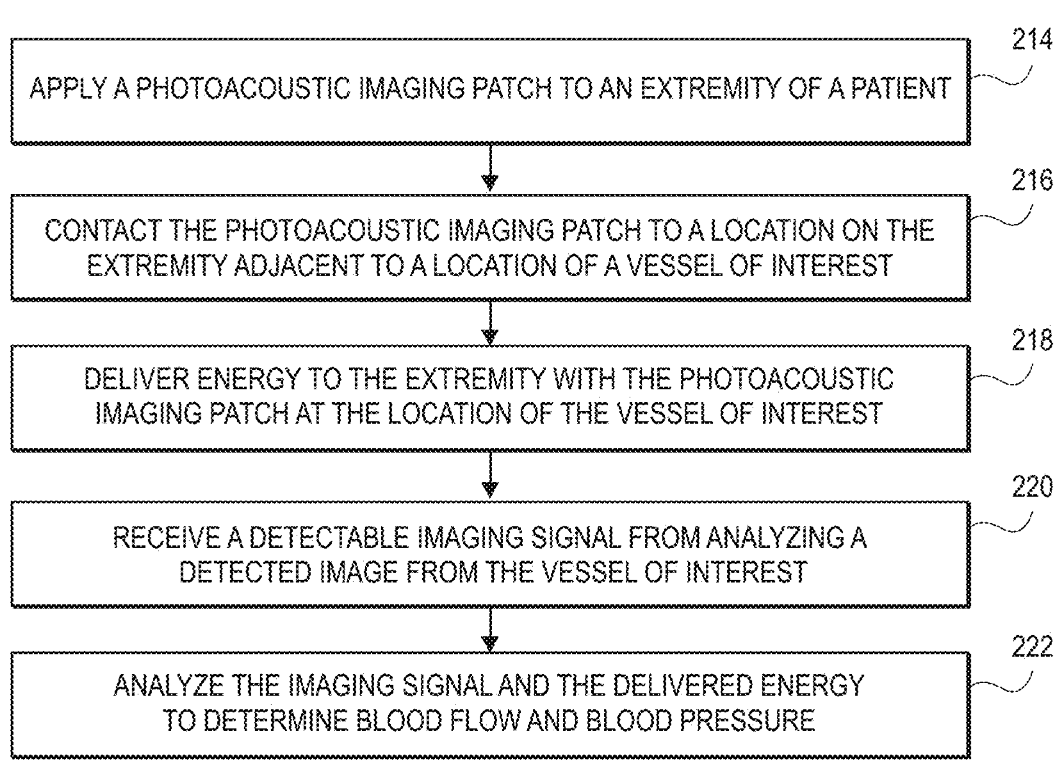
FIG. 2B is a flowchart illustrating an automated method of monitoring blood pressure using photoacoustic detection, according to an embodiment.

FIG. 2A is a flowchart illustrating an automated method of monitoring blood pressure using photoacoustic detection, according to an embodiment. As illustrated in FIG. 2A, the method of automatically measuring blood pressure 200, begins with a step to apply a photoacoustic imaging band to an extremity of a patient 202, and contacting the photoacoustic imaging band to a location on the extremity adjacent to a location of a vessel of interest 204. Next, the method of automatically measuring blood pressure 200 includes a step to deliver energy to the extremity with the photoacoustic imaging band at the location of the vessel of interest 206. Next, a detectable imaging signal is received from analyzing a detected image from the vessel of interest 208, and the final step is to analyze the imaging signal and the delivered energy to determine blood flow and blood pressure 210. According to certain embodiments of the method for automatically measuring blood pressure 200 include placing the photoacoustic imaging band in a location at, adjacent to, near, over or in proximity to a brachial artery. Still other embodiments of the method for automatically measuring blood pressure 200 include placing the photoacoustic imaging band in a location at, adjacent to, near, over or in proximity to a radial artery. In other embodiments of the method for automatically measuring blood pressure 200, other vessels of interest of a patient or other anatomical areas of the patient may be measured. The method for automatically measuring blood pressure 200 may include the measurement of either non-pulsatile flow or pulsatile flow. The method of automatically measuring blood pressure 200, may measure a non-pulsatile flow or a pulsatile flow with a sphygmometer cuff also attached to the extremity of a patient, adjacent to the photoacoustic imaging band. In still other embodiments, the method for automatically measuring blood pressure 200 may include receiving, analyzing, or calculating a pulse wave velocity signal or a continuous wave signal. The method of automatically measuring blood pressure 200 may include measuring blood flow, pulse oximetry, hemoglobin, changes in blood pressure size, or a combination thereof. Alternate embodiments of the method of automatically measuring blood pressure 200 may include estimating stroke volumes, cardiac output, systemic vascular resistance, pulse pressure variation, systolic pressure variation, or a combination thereof using waveform analysis. Machine or computer processor analysis may be necessary to provide numbers, vital sign information, or data. In certain embodiments, the analysis is further capable of outputting a mean or average blood pressure, diastolic bp, MAP based on the pressure at which flow returns, or other vital signs of the patient, as mentioned and described herein. Exemplary embodiments of this method may be capable of measuring these aforementioned vital signs under non-pulsatile flow or under pulsatile flow. The output data or measurement may be exported to a file or readout or output to a visual display of an ultrasound image or a waveform in certain embodiments. In alternative embodiments the data may be output to various categories of patient information, distinguishable by data transmitted or directed to an individual responsible for primary care, such as a medical doctor or specialist, or data directed to an individual responsible for secondary care such as nursing or aid staff or the individual patient. In still other embodiments, a threshold level, such as a narrowing pulse pressure or low blood pressure reading, may trigger an alarm or cue to either a primary or secondary care individual for a potential intervention or further attention.

FIG. 2B is a flowchart illustrating an automated method of monitoring blood pressure using photoacoustic detection, according to an embodiment. As illustrated in FIG. 2B, a method of automatically measuring blood pressure 212, begins with a step to apply a photoacoustic imaging patch to an extremity of a patient 214, and to contact the photoacoustic imaging patch to a location on the extremity adjacent to a location of a vessel of interest 216. The patch may be affixed to a patient onto the extremity with the use of a temporary adhesive. Next, an energy is delivered to the extremity with the photoacoustic imaging patch at the location of the vessel of interest 218, a detectable imaging signal is received from analyzing a detected image from the vessel of interest 220, and the final step is to analyze the imaging signal and the delivered energy to determine blood flow and blood pressure 222. The method of automatically measuring blood pressure 212 may include measuring blood flow, pulse oximetry, hemoglobin, changes in blood pressure size, or a combination thereof. Alternate embodiments of the method of automatically measuring blood pressure 212 may include estimating stroke volumes, cardiac output, systemic vascular resistance, pulse pressure variation, systolic pressure variation, or a combination thereof using waveform analysis. Analysis, measurement, computation or mathematical derivation may be conducted by a machine or computer processor to provide patient vital signs or other data. In certain embodiments, the analysis is further capable of outputting a mean or average blood pressure, diastolic bp, MAP based on the pressure at which flow returns, or other vital signs of the patient as described herein. The output data or measurement may be exported or transmitted to a file or readout or output to a visual display of an image or a waveform representing vessel diameter and flow in certain embodiments. In alternative embodiments the data may be output to various categories of patient information, distinguishable by data directed to an individual responsible for primary care, such as a medical doctor or specialist, or data directed to an individual responsible for secondary care such as nursing or aid staff or the individual patient. In still other embodiments, a threshold level, such as a narrowing pulse pressure or low blood pressure reading, may trigger an alarm or cue to either a primary or secondary care individual for a potential intervention or further attention. In certain embodiments, the foregoing methods may be coupled with either ultrasound or photoacoustic detectors. Ultrasound may be performed at either high frequency or standard frequency, as normally used in ultrasound applications.

An exemplary example of a method of automatically measuring blood pressure and flow includes applying a photoacoustic imaging band to an extremity or neck of a patient. The method of automatically measuring blood pressure also includes contacting the photoacoustic imaging band to a location on the extremity adjacent to a location of a vessel of interest. The method of automatically measuring blood pressure also includes delivering energy to the extremity with the photoacoustic imaging band at the location of the vessel of interest. The method of automatically measuring blood pressure also includes receiving a detectable imaging signal from analyzing a detected image from the vessel of interest, and analyzing the imaging signal and the delivered energy to determine blood flow and blood pressure.

Implementations may include where the location on the extremity is overlying a presumed location of a brachial artery or a presumed location of a radial artery. The method of automatically measuring blood pressure may include measuring a non-pulsatile flow and pressure with a sphygmometer cuff. The method of automatically measuring blood pressure may include measuring a pulsatile flow and pressure with a sphygmometer cuff. The method of automatically measuring blood pressure may include measuring a non-pulsatile pressure with a tonometer. The method of automatically measuring blood pressure may include measuring a pulsatile pressure and flow with a tonometer. The method of automatically measuring blood pressure and blood flow may include receiving a pulse wave velocity signal or receiving a continuous wave signal. The method of automatically measuring blood pressure and flow may include transmitting blood pressure information to an external device. The method of automatically measuring blood pressure and flow may include measuring blood flow, pulse oximetry, hemoglobin, changes in blood vessel size, or a combination thereof, or estimating stroke volumes, cardiac output, systemic vascular resistance, pulse pressure variation, systolic pressure variation, or a combination thereof using waveform analysis. Further, utilization of this technique and apparatus for measuring unilateral or bilateral carotid or middle cerebral arterial blood flow for estimating cerebral blood flow.

A method of automatically measuring blood pressure is disclosed, including applying a photoacoustic imaging patch to an extremity of a patient, including the neck or head. The method of automatically measuring blood pressure also includes contacting the photoacoustic imaging patch to a location on the extremity adjacent to a location of a vessel of interest. The method of automatically measuring blood pressure also includes delivering energy to the extremity with the photoacoustic imaging patch at the location of the vessel of interest. The method also includes receiving a detectable imaging signal from analyzing a detected image from the vessel of interest and analyzing the imaging signal and the delivered energy to determine blood flow and blood pressure.

Exemplary embodiments of methods herein may be capable of measuring these aforementioned vital signs under non-pulsatile flow or under pulsatile flow. Further estimates of cardiac output, cardiac index, SVR, or SVR index based on the application of a non-occlusive pressure reading may be measured using this method. The output data or measurement may be exported or transmitted to a file or readout or output to a visual display of an ultrasound image or a waveform in certain embodiments. In alternative embodiments the data may be output to various categories of patient information, distinguishable by data directed to an individual responsible for primary care, such as a medical doctor or specialist, or data directed to an individual responsible for secondary care such as nursing or aid staff or the individual patient. In still other embodiments, a threshold level, such as a narrowing pulse pressure or low blood pressure reading, may trigger an alarm or cue to either a primary or secondary care individual for a potential intervention or further attention. In certain embodiments, the method utilizing photoacoustic measurements may provide simultaneous vital sign monitoring, including temperature, heart rate, blood pressure, pulse oximetry, or combinations thereof. Furthermore, photoacoustic measurements may also provide potential for measurement of arterial or vessel imagery, via the application of known pressure to detect blood pressure based on a derivation from diameter of the vessel. Certain embodiments may include the use of lasers or even halogen, or LED lights, which can penetrate up to 3 cm of depth. The LED, laser and photoacoustic measurements may also require the appropriate, corresponding receiver or receivers as part of the method or device disclosed herein. Embodiments including photoacoustic imaging transducers may include a light source that, coupled with illumination optics, provides a steady or pulsed supply of optical energy to the targeted vessel to be imaged, one or more ultrasound detectors measuring the generated sound waves or color flow imaging information around the targeted vessel, and one or more signal processing and/or reconstruction units that displays a readable or translatable image. Additional processing units or computer processing devices may be incorporated into the devices or methods herein. In certain embodiments, the foregoing methods may be coupled with either ultrasound or photoacoustic detectors. Ultrasound may be performed at either high frequency or standard frequency, as normally used in ultrasound applications.

In various embodiments, the apparatus and methods described herein may include a computer readable medium comprising instructions which, when executed by at least one electronic processor, configure the at least one electronic processor to execute one or more of the methods or individual steps of methods for automated measurement of blood pressure. Certain embodiments can further include a software or hardware application to allow a user to control the electronic processor. The software application can be, for example, a non-transitory computer readable medium storing instructions, that when executed by a hardware processor, performs a method of providing a graphical user interface on the display to allow a user to control various options for measurements or displayed information. Optionally, the software application can automatically substitute alternate steps, calculations, or output parameters based on attached accessory devices, such as a sphygmometer cuff, tonometer, photoacoustic transducer, or other pressure inducing device element as described previously herein. The method may further includes receiving an input by a user or a request generated by a user. Instructions can then be provided to operate one or more measurement algorithms to be run by the electronic processor, and a display of information intended for a primary care individual or a secondary care individual or a patient may be generated. The software application or the computer readable medium or electronic processor can then provide further instructions, cues, alarms or other information to a user. Next, a primary or alternate output or display may be transmitted to a display device, and an image representing blood pressure data or other vital signs can be displayed on the display device.

In various embodiments, a hardware configuration may include the computer readable medium which can be used to perform one or more of the processes described above. The hardware configuration may include any type of mobile devices, such as smart telephones, laptop computers, tablet computers, cellular telephones, personal digital assistants, wearable devices, etc. Further, the hardware configuration can include one or more processors of varying core configurations and clock frequencies. The hardware configuration may also include one or more memory devices that serve as a main memory during operations, calculations, or simulations as described herein. For example, during operation, a copy of the software that supports the above-described operations can be stored in one or more memory devices. One or more peripheral interfaces, such as keyboards, mice, touchpads, computer screens, touchscreens, etc., for enabling human interaction with and manipulation of the hardware configuration may also be included. Exemplary hardware configurations can also include a data bus, one or more storage devices of varying physical dimensions and storage capacities, such as flash drives, hard drives, random access memory, etc., for storing data, such as images, files, and program instructions for execution by the one or more processors. One or more network interfaces for communicating via one or more networks, such as Ethernet adapters, wireless transceivers, or serial network components, for communicating over wired or wireless media using protocols may further be included.

Additionally, hardware configurations in certain embodiments can include one or more software programs that enable the functionality described herein. The one or more software programs can include instructions that cause the one or more processors to perform the processes, functions, and operations described herein related to calculations, inputs, simulations, pulsed waveform generation, and combinations thereof. Copies of the one or more software programs can be stored in the one or more memory devices and/or on in the one or more storage devices. Likewise, the data utilized by one or more software programs can be stored in the one or more memory devices and/or on in the one or more storage devices.

Embodiments as described herein provide a significantly improved, automated non-invasive blood pressure monitor. This could serve as alternatives to conventional in-hospital blood pressure cuffs, particularly in intensive care units (ICUs), operating rooms, or recovery areas where frequent, accurate blood pressure measurement is of paramount importance. Furthermore, devices and methods embodied herein include automated blood pressure monitoring capable of specific use in measuring blood pressure in patients with low or non-pulsatile flow, including patients in shock and those with a left ventricular assist device (LVAD) or on veno-arterial extracorporeal membrane oxygenation (VA-ECMO). Intraoperative blood pressure monitoring of patients with LVADs or on ECMO is often labor intensive, invasive, and unreliable. Often, a highly trained clinician medical doctor (MD) or certified registered nurse anesthetist (CRNA) is dedicated to this single measurement for the duration of a procedure while others conduct the rest of the anesthetic or associated treatment procedures. An automated blood pressure monitor for these patients as disclosed herein would have further advantages of liberating costly human resources from this duty.

Any of the foregoing embodiments wherein an image is generated, or a vital sign measurement is mathematically derived may require the use of a computer readable medium. A computer readable medium may include instructions which, when executed by at least one electronic processor, configure the at least one electronic processor to execute a method for deriving blood pressure or other vital sign from the automated blood pressure monitoring apparatus as described herein. Certain embodiments can further include a software or hardware application to allow a user to control the electronic processor. The software application can be, for example, a non-transitory computer readable medium storing instructions, that when executed by a hardware processor, performs a calculation or estimate to populate a graphical user interface on a display to allow a user to control various readouts or displays of various vital sign information pertaining to a patient. This data, estimate, or calculation may be received via a wired connection or via a transmitted data stream. The software application or the computer readable medium or electronic processor can then provide instructions to the display or provide user instructions or options for alternate display information. Next, an output of the simulation, calculations, visual representations, or data outputs may be transmitted to an external device or display device.

In various embodiments, a hardware configuration may include the computer readable medium which can be used to perform one or more of the processes described above. The hardware configuration may include any type of mobile devices, such as smart telephones, laptop computers, tablet computers, cellular telephones, personal digital assistants, etc. Further the hardware configuration can include one or more processors of varying core configurations and clock frequencies. The hardware configuration may also include one or more memory devices that serve as a main memory during operations, calculations, or simulations as described herein. For example, during operation, a copy of the software that supports the above-described operations can be stored in one or more memory devices. One or more peripheral interfaces, such as keyboards, mice, touchpads, computer screens, touchscreens, etc., for enabling human interaction with and manipulation of the hardware configuration may also be included. Exemplary hardware configurations can also include a data bus, one or more storage devices of varying physical dimensions and storage capacities, such as flash drives, hard drives, random access memory, etc., for storing data, such as images, files, and program instructions for execution by the one or more processors. One or more network interfaces for communicating via one or more networks, such as Ethernet adapters, wireless transceivers, or serial network components, for communicating over wired or wireless media using protocols may further be included.

Additionally, hardware configurations in certain embodiments can include one or more software programs that enable the functionality described herein. The one or more software programs can include instructions that cause the one or more processors to perform the processes, functions, and operations described herein related to calculations, inputs, simulations, pulsed waveform generation, and combinations thereof. Copies of the one or more software programs can be stored in the one or more memory devices and/or on in the one or more storage devices. Likewise, the data utilized by one or more software programs can be stored in the one or more memory devices and/or on in the one or more storage devices.

If implemented in software, the functions can be stored on or transmitted over a computer-readable medium as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, or EEPROM. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

While the present teachings have been illustrated with respect to one or more implementations, alterations and/or modifications may be made to the illustrated examples without departing from the spirit and scope of the appended claims. For example, it may be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It may be appreciated that structural objects and/or processing stages may be added, or existing structural objects and/or processing stages may be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. The terms "couple," "coupled," "connect," "connection," "connected," "in connection with," and "connecting" refer to "in direct connection with" or "in connection with via one or more intermediate elements or members." Finally, the terms "exemplary" or "illustrative" indicate the description is used as an example, rather than implying that it is an ideal. Other embodiments of the present teachings may be apparent to those skilled in the art from consideration of the specification and practice of the disclosure herein. It is intended that the specification and examples be considered as exemplary only, with a true scope and spirit of the present teachings being indicated by the following claims.

What is claimed is:

1. A method of automatically measuring blood pressure, comprising:

applying a photoacoustic imaging band comprising a photoacoustic imaging transducer to an extremity of a patient;

contacting the photoacoustic imaging band to a location on the extremity adjacent to a location of a vessel of interest;

measuring a non-pulsatile flow or a pulsatile flow with a sphygmometer cuff also attached to the extremity of the patient, adjacent to the photoacoustic imaging band, wherein a central processing unit inflates the sphygmometer cuff until there is no longer a measurable flow through the vessel of interest, then deflates the sphygmometer cuff until a measurable flow returns;

delivering acoustic energy to the extremity with the photoacoustic imaging transducer at the location of the vessel of interest;

receiving imaging information generated in response to the delivered energy; and computing the acoustic energy;

generating a detectable image of the vessel of interest from the imaging information received from the photoacoustic imaging transducer using the central processing unit, where the detectable image represents the vessel of interest; and analyzing the detectable image and the imaging information with the central processing unit to execute a software application to determine blood flow and blood pressure, wherein the flow patterns are analyzed to determine mean and diastolic blood pressure, and outputting a mean arterial pressure (MAP) based on the pressure at which a measurable flow returns.

2. The method of automatically measuring blood pressure of claim 1, wherein the location on the extremity is overlying a presumed location of a brachial artery.

3. The method of automatically measuring blood pressure of claim 1, wherein the location on the extremity is overlying a presumed location of a radial artery.

4. The method of automatically measuring blood pressure of claim 1, wherein the location on the extremity is overlying a presumed location of a carotid artery.

5. The method of automatically measuring blood pressure of claim 1, wherein the location on the extremity is overlying a presumed location of a cerebral artery.

6. The method of automatically measuring blood pressure of claim 1, further comprising measuring a pulsatile flow with a sphygmometer cuff.

7. The method of automatically measuring blood pressure of claim 1, further comprising receiving a pulse wave velocity signal.

8. The method of automatically measuring blood pressure of claim 1, further comprising receiving a continuous wave signal.

9. The method of automatically measuring blood pressure of claim 1, further comprising transmitting blood pressure information to an external device.

10. The method of automatically measuring blood pressure of claim 1, further comprising measuring blood flow, pulse oximetry, hemoglobin, changes in blood pressure size, or a combination thereof.

11. The method of automatically measuring blood pressure of claim 1, further comprising estimating stroke volumes, cardiac output, systemic vascular resistance, pulse pressure variation, systolic pressure variation, or a combination thereof using waveform analysis.

12. A method of automatically measuring blood pressure, comprising:

applying a photoacoustic imaging patch comprising a photoacoustic imaging transducer to an extremity of a patient;

contacting the photoacoustic imaging patch to a location on the extremity adjacent to a location of a vessel of interest;

measuring a non-pulsatile flow or a pulsatile flow with a sphygmometer cuff also attached to the extremity of the patient, adjacent to the photoacoustic imaging patch, wherein a central processing unit inflates the sphygmometer cuff until there is no longer a measurable flow through the vessel of interest, then deflates the sphygmometer cuff until a measurable flow returns;

delivering acoustic energy to the extremity with the photoacoustic imaging transducer at the location of the vessel of interest;

receiving imaging information generated in response to the delivered acoustic energy; and computing the acoustic energy;

generating a detectable imaging signal of the vessel of interest from analyzing the imaging information using a central processing unit to execute a software application; and analyzing the detectable imaging signal and the delivered acoustic energy to determine blood flow and blood pressure using the central processing unit configured to execute a software application, wherein the flow patterns are analyzed to determine mean and diastolic blood pressure, and outputting a mean arterial pressure (MAP) based on the pressure at which a measurable flow returns.

13. The method of automatically measuring blood pressure of claim 12, wherein the patch is applied to the extremity with the use of a temporary adhesive.

14. The method of automatically measuring blood pressure of claim 12, further comprising measuring blood flow, pulse oximetry, hemoglobin, changes in blood pressure size, or a combination thereof.

15. The method of automatically measuring blood pressure of claim 12, further comprising estimating stroke volumes, cardiac output, systemic vascular resistance, pulse pressure variation, systolic pressure variation, or a combination thereof using waveform analysis.

* * * * *